(12) United States Patent
Perricone

(10) Patent No.: US 6,500,857 B1
(45) Date of Patent: Dec. 31, 2002

(54) SUBCUTANEOUS MUSCLE TREATMENT USING ELECTRONIC STIMULATION AND TOPICAL COMPOSITIONS

(76) Inventor: Nicholas V. Perricone, 27 Coginchaug Ct., Guilford, CT (US) 06437

( * ) Notice: Subject to any disclaimer, the term of this patent is extended or adjusted under 35 U.S.C. 154(b) by 0 days.

(21) Appl. No.: 09/931,616

(22) Filed: Aug. 16, 2001

(51) Int. Cl.$^7$ .................... A61K 31/385; A61K 31/195; A61K 7/48; A61K 7/42
(52) U.S. Cl. .................. 514/440; 514/561; 514/669; 514/474; 514/944; 514/785; D24/200; 424/401; 424/59; 424/450
(58) Field of Search .................. 514/440, 561, 514/667, 474; 424/401, 59, 450; D24/200; D29/114

(56) References Cited

U.S. PATENT DOCUMENTS

| | | | |
|---|---|---|---|
| 3,387,147 A | 6/1968 | Radwin | |
| 3,851,651 A | 12/1974 | Icenbice | |
| 4,062,364 A | 12/1977 | Kameny | |
| 5,554,647 A | 9/1996 | Perricone | |
| 5,643,586 A | * 7/1997 | Perricone | 424/401 |
| 5,709,868 A | * 1/1998 | Perricone | 424/401 |
| 5,879,690 A | 3/1999 | Perricone | |
| 6,162,419 A | * 12/2000 | Perricone | 424/59 |
| 6,319,942 B1 | * 11/2001 | Perricone | 514/440 |

OTHER PUBLICATIONS

"Perricone Alpha Lipoic Acid: Common Questions", Clinical Creations, www.veinlase.com, 1999.*
"N.V. Perricone, M.D. Cosmeceuticals Alph Lipoic Acid and Vitamin C Ester Skin Care", www.skincarerx.safeserver.com, 1999.*
Flextone Internet Information, www.flextone.com/tech-data,html, freq-quest.html, pad-place.html, usses.html, 2000.

* cited by examiner

Primary Examiner—Zohreh Fay
Assistant Examiner—Brian-Yong Kwon
(74) Attorney, Agent, or Firm—Mary M. Krinsky

(57) ABSTRACT

Aging and sagging subcutaneous muscles are treated by first applying a composition containing at least one acetylcholine precursor and/or at least one compound exhibiting catecholamine activity to the overlying skin area, and then electronically stimulating the overlying skin area using electrical pulses in amounts sufficient to cause the subcutaneous muscles to contract. Preferred compositions contain from about 1% to about 10%, more narrowly from about 0.25% to about 5% by weight of an alkanolamine such as dimethylaminoethanol, the calcium salt of 2-aminoethanol phosphate or mixtures thereof and about from about 1% to about 10%, more narrowly from about 1% to 5% by weight of a compound exhibiting catecholamine activity such as tyrosine. Preferred electronic muscle stimulating devices deliver electrical pulses via electrodes in the fingertips of a compact device that fits on the hand.

19 Claims, No Drawings

US 6,500,857 B1

SUBCUTANEOUS MUSCLE TREATMENT USING ELECTRONIC STIMULATION AND TOPICAL COMPOSITIONS

STATEMENT REGARDING FEDERALLY SPONSORED RESEARCH

Not Applicable

BACKGROUND OF THE INVENTION

1. Field of the Invention

This invention relates primarily to the treatment of subcutaneous muscles and overlying skin, particularly for faces that have developed prominent lines such as the nasolabial folds, hanging of tissue from the mandibular region, and increased sagging of tissue around the eyes observed in aging and other conditions such as myasthenia gravis, but also for the treatment of other bodily areas wherein sagging is observed, such as in the chest and breast region, and the upper arms and legs. The invention provides methods for treating subcutaneous muscles and the overlying epidermis to ameliorate these changes, and improve a person's external appearance. It also provides methods for preserving a person's youthful appearance.

2. Description of Related Art

The external wrinkled appearance of aging individuals is caused by changes in both epidermal tissue and subcutaneous changes in muscle tissue. In aging, the epidermis thins and skin appendages atrophy. Hair becomes sparse and sebacious secretions decrease, with consequent susceptibility to dryness, chapping, and fissuring. The regularity of tissue structure is lost, and individual cells enlarge, but the total number of cells decreases approximately 30%. Intercellular collagen and elastin increases. The proportion of soluble collagen decreases, and there may be increased cross-linking between long-chain collagen macromolecules. Elastin loses its discrete structure and elasticity and has an increased calcium content.

Changes in underlying muscle tissue accompany changes in the epidermis. When muscles are at rest, a certain amount of tautness usually remains. The residual degree of contraction in skeletal muscles is called muscle tone. In aging individuals, the degree of contraction relaxes. The effects of gravity and lengthening muscles give a sagging appearance, which is particularly obvious in the face.

Previous treatments of flaccid skin and muscles from aging typically involved plastic surgery. The plastic surgeon cuts the skin and muscle and then pulls it taut, reducing some of the tissue and discarding it, then suturing it so that the facial, chest, arm, leg, and/or buttocks muscles remain tight. More recently, I suggested the use of topical compositions that penetrate the skin and shorten subcutaneous muscles, resulting in a lift in tissue on the face, chest, upper arms, upper legs or other areas of application, while at the same time improving the overall condition of the overlying skin. The compositions contain acetylcholine precursors such as alkanolamines and/or ingredients that produce catecholamine activity such as catecholamines and related compounds, alone or in combination with other ingredients and percutaneous penetration enhancers (U.S. Pat. Nos. 5,554,647 and 5,879,690 to Perricone; these patents and others cited hereafter are expressly incorporated herein in their entireties by reference). While not wishing to be bound to any theory, these active ingredients seem to cause muscle contraction biochemically as described in my patents.

It would be desirable to provide treatments that augment topical compositions and reverse or diminish the effects of aging without cosmetic surgery, and to treat other conditions exhibiting sagging muscles such as those observed in myasthenia gravis.

BRIEF SUMMARY OF THE INVENTION

It is an objective of the invention to provide new methods for the treatment of aging and sagging skin and subcutaneous muscle tissue. This is achieved by topically applying to overlying skin areas a composition containing at least one acetylcholine precursor such as an alkanolamine and/or at least one compound having catecholamine activity and then electronically stimulating the area with a muscle stimulator for a time sufficient to cause an observable increase in muscle tone. Preferred embodiments employ both an acetylcholine precursor such as dimethylaminoethanol or the calcium salt of 2-aminoethanol phosphate and a compound having catecholamine activity such as tyrosine, phenylalanine, dopa, or serotonin in the topical composition. Many embodiments also contain adjunct ingredients such as $\alpha$-hydroxy acids (e.g., glycolic acid), a fatty acid ester of ascorbic acid (e.g., ascorbyl palmitate), and/or lipoic acid. Electronic stimulation is affected in preferred embodiments using a hand device that delivers subcutaneous muscle stimulation through electrodes in the fingertips.

BRIEF DESCRIPTION OF THE INVENTION

This invention is based upon the finding that electronic workout devices and electrical muscle stimulators used by sports trainers, professional athletes, and physical therapists, and a muscle stimulator I designed that has electrodes in the fingertips of a device that fits on the hand, can be used in combination with my topical compositions to provide increased muscle tone that lifts tissue on the face, chest, or other areas where the treatment is applied, resulting in a more youthful appearance. Using electronic muscle stimulators in combination with my previously described topical compositions appears to simultaneously enhance neurotransmission while at the same time muscular contractions, significantly increasing and optimizing muscle contraction, resulting in pronounced cosmetic benefits.

In the practice of the invention, a topical composition containing at least one acetylcholine precursor and/or at least one compound exhibiting catecholamine activity is applied to aging and sagging skin areas, and then electrical pulses sufficient to cause subcutaneous muscles to contract are applied to the areas. In most embodiments, the compositions applied before use of a muscle stimulating device contain adjunct ingredients such as an $\alpha$-hydroxy acid, a fatty acid ester of ascorbic acid, lipoic acid or a lipoic acid derivative, or mixtures of any of these. Typical stimulators deliver pulses having a relatively high voltage-to-width ratio and a steep waveform to achieve optimal muscle contraction without discomfort.

By the term "acetylcholine precursor" is meant any precursor in the bio-synthetic pathway of acetylcholine, or related pathways. These include co-factors and precursors of acetylcholine, synthetic enzymes and precursors or enhancers of acetyl production. Acetylcholine precursors include, but are not limited to, alkanolamines of the formula

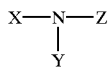

wherein X, Y and Z are selected from the group consisting of hydrogen, $C_1$–$C_3$ alkyl groups, $C_2$–$C_4$ alkanol group, wherein at least one of X, Y, or Z is a $C_2$–$C_4$ alkanol group bearing at least one hydroxyl group and optionally at least one carboxyl group, acetic acid esters of diethylaminoethanol, acetic acid esters of monomethylaminoethanol, para-chlorophenylacetic acid esters of monoaminoethanol, para-chlorophenylacetic acid esters of dimethylaminoethanol, physiologic salts of 2-aminoethanol phosphate, and mixtures thereof. Useful acetylcholine precursor compounds for the invention include, but are not limited to, ethylaminoethanol, methylaminoethanol, dimethylaminoethanol, isopropanolamine, triethanolamine, isopropanoldimethylamine, ethylethanolamine, 2-butanolamine, choline, serine, the calcium salt of 2-aminoethanol phosphate, the sodium salt of 2-aminoethanol phosphate, the potassium salt of 2-aminoethanol phosphate, and mixtures thereof. Many preferred embodiments employ methylaminoaminoethanol, dimethylaminoethanol, ethylaminoethanol, the calcium salt of 2-aminoethanol phosphate, and/or triethanolamine; particularly preferred is dimethylaminoethanol (DMAE) and/or the calcium salt of 2-aminoethanol phosphate.

In addition to, or instead of, acetylcholine precursors, topical compositions applied prior to electronic muscle stimulation contain at least one compound that exhibits catecholamine activity, i.e., a catecholamine, a catecholamine-related compound and/or a catecholamine mimic. By "catecholamine" is meant any one of a group of amines that act upoon nerve cells as neurotransmitters or hormones. This group of similar compounds having a sympathomimetic action typically are molecules having an aromatic portion derived from catechol (2-hydroxyphenol) and an aliphic amine portion. Catecholamines include, but are not limited to, dopamine (5-hydroxytryptamine), norepinephrine (noradrenaline; 4-(2-amino-1-hydroxyethyl)-1,2-benzenediol), and epinephrine (adrenaline; 4-(1-hydroxy-2-(methylamino)ethyl)-1,2-benzenediol). As used herein, dopa (3,4-dihydroxyphenylalanine) and serotonin (5-hydroxytryptamine) are also included in this group.

Catecholamine-related compounds include catecholamine precursors, catecholamine mimics, chemicals that augment the release of catecholamines, and mixtures of these with each other and with catecholamine. Catecholamine precursors include any in the synthetic pathway such as, for example, tyrosine, dopa, phenylalanine, and mixtures thereof. Tyrosine is particularly preferred. Catecholamine mimics include, but are not limited to, sympathomimetic amines that function similarly, augmenting, for example, the release of norepinepherine, such as tyramine, ephedrine, amphetamine, and mixtures thereof. Chemicals that augment the release of catecholamines specifically include those that augment release such as co-factors of enzymes in the metabolic pathway, e.g., tetrahydrobiopterin and pyridoxine, as well as inhibitors of enzymes that inactive catecholamines such as inhibitors of catechol-O-methyltransferase and monoamine oxidase. Preferred embodiments employ compositions that contain both at least one acetylcholine precursor and at least one compound that exhibits catecholamine activity.

Only effective amounts of active ingredients are needed to enhance the action of the muscle stimulator, so generally topical application is accomplished in association with a carrier, and particularly one in which the active ingredients are soluble per se or is effectively solubilized (e.g., as an emulsion or microemulsion). Where employed, the carrier is inert in the sense of not bringing about a deactivation or oxidation of the compounds, and in the sense of not bringing about any adverse effect on the skin areas to which it is applied. In one preferred practice of the invention, active ingredients are applied in admixture with a dermatologically acceptable carrier or vehicle (e.g., as a lotion, cream, ointment, soap, stick, or the like) so as to facilitate topical application and, in some cases, provide additional therapeutic effects as might be brought about, e.g., by moisturizing of the affected skin areas. While the carrier for dermatological compositions can consist of a relatively simple solvent or dispersant such as water, it is generally preferred that the carrier comprise a composition more conducive to topical application, and particularly one which will form a film or layer on the skin to which it is applied so as to localize the application in areas that will be electrically stimulated and/or aid in the percutaneous delivery of the active agent.

Many preparations are known in the art, and include lotions containing oils and/or alcohols and emollients vegetable oils, hydrocarbon oils and waxes, silicone oils, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. One preferred embodiment is an oil-in-water cream. Such compositions are referred to herein as dermally or dermatologically acceptable carriers, and are formulated using conventional techniques known to those of ordinary skill in the art.

Suitable carriers include water, alcohols, oils and the like, chosen for their ability to dissolve or disperse active ingredients and any other adjunct ingredients used in the treatment. Many embodiments contain from about 0.1% to about 10% by weight, more narrowly from about 0.25% to about 5% to 7% by weight, and in many cases from about 1% to about 3% by weight, alkanolamine such as dimethylaminoethanol in the total composition, and/or from about 0.1% to 10% by weight, more narrowly from about 0.25% to about 7%, even more narrowly, from about 1% to 5%, catecholamine or related compound such as tyrosine. To maximize muscle toning, it is desirable that the topically applied composition be formulated to contain at least about 1% by weight alkanolamine and at least about 1% catecholamine compound, and many embodiments contain more than 1 weight % of each ingredient. One efficacious embodiment contains from about 2% to about 5% by weight alkanolamine and from about 2% to about 5% catecholamine compound. In embodiments containing tyrosine, it is typically present in amounts ranging from about 0.01% to about 5%, more preferably from about 0.04% to about 3% by weight, and most preferably about 0.5% by weight, based on the total composition.

Generally in the practice of methods of the invention, the composition topically applied prior to using a muscle stimulating device contains adjunct ingredients in addition to the acetylcholine precursor and/or catecholamine active ingredients. Adjunct ingredients include, but are not limited to, lipoic acid or a lipoic acid derivative, α-hydroxy acids, and fatty acid esters of ascorbic acid. Many embodiments employ more than one adjunct ingredient. Where employed, adjunct ingredients are anticipated to have additive effects if not synergistic effects due to different mechanisms of action.

A preferred adjunct ingredient is lipoic acid or a lipoic acid derivative. As described in one of my patents (U.S. Pat. No. 5,709,868 to Perricone), topically applied lipoic acid is efficacious for the prevention and/or treatment of skin damage, particularly inflammation and aging. As used herein, the term "lipoic acid" encompasses thioctic acid (1,2-dithiolane-3-pentanoic acid; 1,2-dithiolane-3-valeric acid), $C_8H_{14}O_2S_2$, formula weight 206.32, and biologically equivalent lipoic acid derivatives, including dihydrolipoic acid and particularly efficacious derivatives that exhibits increased cellular uptake and biological activity such as N,N-dimethyl, N-2-amidoethyl lipoate.

Lipoic acid derivatives include thioctic acid esters, particularly alkyl esters such as fatty acid esters, amides, particularly those isolated from or mimicking naturally occurring lipoamides, salts, particularly alkali metal salts, anhydrides and specifically includes the reduced form, dihydrolipoic acid and its esters, amides and salts. Since lipoic acid is both fat- and water-soluble, it is an advantage of the invention that it can be used in either lipid or aqueous-based compositions, and it readily crosses cellular membranes and disperses in extracellular and intracellular tissue components. Derivatives may also include those involving other reactive groups known to those skilled in the art. As used herein, the term "derivatives" includes metabolic precursors of lipoic acid. Where lipoic acid derivatives are employed, they must be functionally equivalent to lipoic acid. In typical embodiments of the invention containing lipoic acid or a lipoic acid derivative as an adjunct ingredient, the composition contains from about 0.1% to about 7 weight %, lipoic acid or dihydrolipoic acid. In one embodiment, about 2% to 3% lipoic acid is employed with the active muscle tone-enhancing ingredients.

An alternate or additional adjunct ingredient is at least one α-hydroxy acid or an α-hydroxy acid iderivative. As used herein, the term "α-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Preferred α-hydroxy acids and/or α-hydroxy acid derivatives are less bulky structurally so that they penetrate the skin well, and thus have a backbone of from one to three carbon atoms such as those set out my U.S. Pat. No. 5,965,618 at column 6 lines 4 to 29. Where employed, glycolic and/or lactic acid or their derivatives are preferred; glycolic acid is especially efficacious. Glycolic acid or other α-hydroxy acid is typically present in amounts ranging from about 1% to about 10%, more narrowly from about 3% to about 7% of the total composition.

Fat-soluble fatty acid esters of ascorbic acid (vitamin C) are employed as an adjunct ingredient in some embodiments, alone or in combination with a lipoic acid or an α-hydroxy acid ingredient. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate. It is an advantage of the invention that where fatty acid esters of ascorbic acid are employed as an adjunct ingredient, they help stabilize other ingredients in the composition. Ascorbyl palmitate and the like ascorbyl esters are typically present in amounts ranging from about 0.5% to about 15%, preferably from about 1% to about 7% to 10%, of the total composition.

Topical compositions of the invention can comprise additional ingredients commonly found in skin care compositions, such as, for example, emollients, skin conditioning agents, emulsifying agents, humectants, preservatives, antioxidants, perfumes, chelating agents, etc., provided that they are physically and chemically compatible with other components of the composition. Preservatives include, but are not limited to, $C_1-C_3$ alkyl parabens and phenoxyenthanol, typically present in an amount ranging from about 0.5% to about 2.0% by weight percent, based on the total composition. Emollients, typically present in amounts ranging from about 0.01% to 5% of the total composition include, but are not limited to, fatty esters, fatty alcohols, mineral oils, polyether siloxane copolymers, and mixtures thereof. Humectants, typically present in amounts ranging from about 0.1% to about 5% by weight of the total composition include, but are not limited to, polyhydric alcohols such as glycerol, polyalkylene glycols (e.g., butylene glycol, propylene glycol, dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, and mixtures thereof. Emulsifiers, typically present in amounts from about 1% to about 10% by weight of the composition, include, but are not limited to, stearic acid, cetyl alcohol, stearyl alcohol, steareth 2, steareth 20, acrylates/$C_{10-30}$ alkyl acrylate crosspolymers, and mixtures thereof. Chelating agents, typically present in amounts ranging from about 0.01% to about 2% by weight, include, but are not limited to, ethylenediamine tetraacetic acid (EDTA) and derivatives and salts thereof, dihydroxyethyl glycine, tartaric acid, and mixtures thereof.

Antioxidants, typically present in an amount ranging from about 0.02% to about 0.5% by weight of the composition, include, but are not limited to, butylated hydroxy toluene (BHT); vitamin C and/or vitamin C derivatives, such as fatty acid esters of ascorbic acid, particularly asocorbyl palmitate; butylated hydroanisole (BHA); phenyl-a-naphthylamine; hydroquinone; propyl gallate; nordihydroquiaretic acid; vitamin E and/or derivatives of vitamin E, including tocotrienol and/or tocotrienol derivatives; calcium pantothenates; green tea extracts; mixed polyphenols; and mixtures of any of these. As mentioned above, particularly preferred antioxidants are those that provide additional benefits to the skin such as ascorbyl palmitate. (See additional ingredients and methods in my U.S. Pat. Nos. 4,775,530, 5,376,361, 5,409, 693, 5,545,398, 5,574,063, 5,643,586, 5,709,868, 5,879,690, 5,965,618, 5,968,618, 6,051,244, 6,142,419, 6,162,419, and 6,191,121, all to Perricone).

Buffering agents are employed in many compositions. Preferably, the amount of buffering agent is one that results in compositions having a pH ranging from about 4.5 to about 8.5, more preferably from about 5.5 to about 8.5, most preferably from about 6.5 to about 8.0. Typical buffering agents are chemically and physically stable agents commonly found in cosmetics, and can include compounds that are also adjunct ingredients such as citric acid, malic acid, and glycolic acid buffers.

Typical compositions of the invention comprise from about 1% to about 10%, more narrowly from about 0.25% to about 5% by weight, and even more narrowly from about 1% to about 3% by weight dimethylaminoethanol and/or the calcium salt of 2-aminoethanol phosphate, and from about 1% to about 5%, preferably about 3% by weight, tyrosine. In many embodiments, the composition further comprises from about 0.25% to about 5%, more narrowly from about 1% to about 3% by weight, lipoic acid; from about 3% to about 7% by weight glycolic acid; and from about 1% to about 7% by weight ascorbyl palmitate.

After topical application of compositions of the invention to sagging or aging skin areas, subcutaneous muscles are electronically stimulated using an electrically operable stimulator, typically with electrical pulses sufficient to cause the muscles to contract and result in a clinically perceptable increase in subcutaneous muscle tone. Any previously decribed muscle stimulating device such as that used by athletes and their trainers and physical therapists may be used, and facial exercisers are particularly preferred. (See, for example U.S. Pat. No. 3,861,651 to Icenbice, U.S. Pat. No. 3,387,147 to Radwan, and U.S. Pat. No. 4,062,365 to Kameny.) These employ batteries or wall current, and typically comprise terminals applied to affected skin areas attached to a regulating device, but facial masks containing electrodes may also be employed.

Optimum stimulation typically requires pulses having a relatively high voltage-to-width ratio and a steep waveform. High voltage, wide-width pulses having a low rising wave front produce undesirable stinging sensations. Low voltage, wide-width pulses do not induce proper muscular contraction. Preferred devices provide a pulse output having an adjustable amplitude level to suit the needs of the individual user; these ordinarily exhibit a sharp rising voltage waveform of an optimum width to induce proper muscle contractions. Most devices comprise at least three electrodes, but one or two will suffice, and the number may be extended to any desired number. Preferred individual pulses have a total duration not over a few seconds, preferably not over about 5 seconds, and optimally between about one-fourth of a second and 2 seconds, delivering an output current of up to about 120 mA, but lower or higher pulses varying frequency, pulse width, intensity and pulse signals can be used to control the amount and strength of the impulses as described by the device manufacturer. (See, for example, FlexTONE™ instructions at http://www.flextone.com.) Commercially available muscle stimulators include, but are not limited to, Derma-Tone™ facial exercisers and Flex-TONE™ electronic muscle stimulators. After a pulse, there is a rest period of a duration not over a few seconds, preferably not over about 10 seconds, and optimally between about one-half and four seconds, when there is no output current.

The peak-to-peak current delivery mimics the natural brain stimulation of muscle tissue, delivering gentle electrical pulses to the muscles, causing them to contract and then relax, as if the message were coming from the brain. An advantage of the invention is that it mimics nature. Also electronic muscle stimulation not only improves subcutaneous muscle tone as part of the anti-aging treatment and provides cosmetic benefits by improving an individual's appearance, but muscle stimulation often provides relief from minor pain, tiredness, and stress, contributing to an overall relaxed and refreshed feeling after treatment.

I have designed a muscle stimulator that delivers appropriate electrical pulses using electrodes in the fingertips of a device that fits on the hand (U.S. Des. Ap. Nos. 29/148,565, 29/148,554, and 29/151,068). One embodiment is a glove; another uses fingertip covers. The design allows for efficient and easy application of electrical stimuli to whatever regions of the body the user desires, without the cumbersome attachment of current terminals or electrodes. Treatment cycles are conveniently short. The device is compact, portable, and lightweight. Simple designs by others may also be employed; see, for example the facial exercisers depicted in U.S. Des. Pat. No. 282,949 to Arve and U.S. Des. Pat. No. 397,173 to Edell.

An important advantage of the invention is the synergy provided by using electronic subcutaneous muscle stimulation together with biochemical subcutaneous muscle stimulation caused by topical application of acetylcholine precursors and/or catecholamine compounds, preferably both. Simultaneously providing neurotransmitter precursors and electrical pulses results in greater muscle tightening and toning than what is achieved by using either electronic or biochemical stimulation alone or by using electronic or biochemical stimulation sequentially. The result is a more youthful appearance to the skin and the body areas to which the treatment is applied, shaping and toning. This is particularly true of the face. The combination treatment decreases wrinkles, and firms nasolabial folds; the mandibular region, and sagging around the eyes, resulting in a smoother, tighter, more youthful appearance. Patients benefit not only from favorable cosmetic effects using the treatment, but also find the treatment contributes to an overall relaxed and refreshed feeling. Over time, the muscles actually appear to shorten so that persons using the treatment look as though they've had a facelift or other cosmetic surgery. And the therapy can be easily managed by an individual alone at home or at a health club or gym, and the like, without cumbersome equipment, prescription drugs, or surgery. No assistance from a physician or other technical person is required to operate the equipment, and the composition ingredients are safe. Insofar as has been determined to date, no adverse side effects are encountered.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for stimulating subcutaneous muscles and increasing subcutaneous muscle tone comprising (I) first topically applying to overlying skin area a composition which comprises
    (a) an acetylcholine precursor active ingredient selected from the group consisting of an alkanolamine of the formula

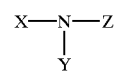

wherein X, Y and Z are selected from the group consisting of hydrogen, $C_1$–$C_3$ alkyl groups, $C_2$–$C_4$ alkanol group, wherein at least one of X, Y, or Z is a C₂–C₄ alkanol group bearing at least one hydroxyl group and optionally at least one carboxyl group, acetic acid esters of diethylaminoethanol, acetic acid esters of monomethylaminoethanol, parachlorophenylacetic acid esters of monoaminoethanol, parachlorophenylacetic acid esters of dimethylaminoethanol, the calcium salt of 2-aminoethanol phosphate, the sodium salt of 2-aminoethanol phosphate, the potassium salt of 2-aminoethanol phosphate, and mixtures thereof; or (b) a compound exhibiting catecholamine activity selected from the group consisting of dopamine, norepinephrine, epinephrine, dopa, serotonin, tyrosine, phenylalanine, tyramine, ephedrine, amnphetamine, tetrahydrobiopterin, pyridoxine, and mixtures thereof; or (c) a combination of at least one said acetylcholine precursor and at least one said compound exhibiting catecholamine activity; and then (II) applying to the overlying skin area electrical pulses sufficient to cause the subcutaneous muscles to contract.

2. A method according to claim 1 wherein the composition contains at least one said acetylcholine precursor and at least one said compound having catecholamine activity.

3. A method according to claim 1 wherein the acetylcholine precursor is selected from the group consisting of diethylaminoethanol, monoaminoethanol, choline, serine, the calcium salt of 2-aminoethanol phosphate and mixtures thereof, and the compound exhibiting catecholamine activity is selected from the group consisting of tyrosine, phenylalanine, serotonin, dopa, pyridoxine, and mixtures thereof.

4. A method according to claim 3 wherein the composition contains diethylaminoethanol, the calcium salt of 2-aminoethanol phosphate, or a mixture of these alkanolamines, and tyrosine.

5. A method according to claim 4 wherein the composition contains from about 1% to about 10% alkanolamine and from about 1% to about 5% by weight tyrosine.

6. A method according to claim 5 wherein the composition contains from about 2% to about 5% by weight alkanolamine and about 3% by weight tyrosine.

7. A method according to claim 1 wherein the electrical pulses are delivered by electrodes in the fingertips of a muscle stimulating device that fits on the hand.

8. A method according to claim 1 wherein the electrical pulses having a relatively high voltage-to-width ratio and a steep waveform.

9. A method according to claim 1 wherein the composition further comprises at least one adjunct ingredient selected from the group consisting of an α-hydroxy acid, a fatty acid ester of ascorbic acid, lipoic acid or a lipoic acid derivative, and mixtures of any of these.

10. A method according to claim 9 wherein the composition comprises glycolic acid, ascorbyl palmitate, and lipoic acid.

11. A method according to claim 10 wherein the composition contains from about 0.25% to about 5% lipoic acid, from about 3% to about 7% by weight glycolic acid, and from about 1% to about 7% ascorbyl palmitate.

12. A method for stimulating subcutaneous muscles and increasing subcutaneous muscle tone comprising first topically applying to overlying skin areas a composition which comprises tyrosine and an alkanolamine selected from the group consisting of dimethylaminoethanol, the calcium salt of 2-aminoethanol phosphate, and mixtures thereof, and then applying to the overlying skin area electrical pulses sufficient to cause the subcutaneous muscles to contract.

13. A method according to claim 12 wherein the composition contains from about 1% to about 10% alkanolamine and from about 1% to about 5% by weight tyrosine.

14. A method according to claim 12 wherein the composition contains from about 0.25% to about 5% by weight alkanolamine and about 3% by weight tyrosine.

15. A method according to claim 12 wherein the composition further comprises at least one adjunct ingredient selected from the group consisting of an α-hydroxy acid, a fatty acid ester of ascorbic acid, lipoic acid or a lipoic acid derivative, and mixtures of any of these.

16. A method according to claim 15 wherein the composition contains from about 0.25% to about 5% lipoic acid, from about 3% to about 7% by weight glycolic acid, and from about 1% to about 7% by weight ascorbyl palmitate as adjunct ingredients.

17. A method according to claim 12 wherein the electrical pulses having a relatively high voltage-to-width ratio and a steep waveform.

18. A method according to claim 12 wherein the electrical pulses are delivered by electrodes in the fingertips of a muscle stimulating device that fits on the hand.

19. A method for stimulating subcutaneous muscles and increasing subcutaneous muscle tone comprising first topically applying to overlying skin areas a composition which comprises about 3% by weight tyrosine and from about 1% to about 3% by weight dimethylaminoethanol, and then applying to the overlying skin area electrical pulses sufficient to cause the subcutaneous muscles to contract and produce an observable increase in muscle tone.

\* \* \* \* \*